(12) United States Patent
Cao et al.

(10) Patent No.: US 6,794,138 B1
(45) Date of Patent: Sep. 21, 2004

(54) METHODS OF SMALL SAMPLE AMPLIFICATION

(75) Inventors: Yanxiang Cao, Mountain View, CA (US); Linda Hsie, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 125 days.

(21) Appl. No.: 09/961,709

(22) Filed: Sep. 24, 2001

Related U.S. Application Data

(63) Continuation-in-part of application No. 09/854,317, filed on May 11, 2001, now Pat. No. 6,582,938, and a continuation-in-part of application No. 09/738,892, filed on Dec. 18, 2000.
(60) Provisional application No. 60/172,340, filed on Dec. 16, 1999.

(51) Int. Cl.⁷ ............................ C12Q 1/68; C12P 19/34; C07H 21/02; C07H 21/04; C07H 19/00
(52) U.S. Cl. ............................ 435/6; 435/7.1; 435/91.1; 435/91.2; 536/22.1; 536/23.1; 536/24.3; 536/24.31; 536/24.32; 536/24.33
(58) Field of Search ............................ 435/6, 7.1, 91.1, 435/91.2; 536/22.1, 23.1, 24.3–24.33

(56) References Cited

U.S. PATENT DOCUMENTS

| 5,130,238 A | 7/1992 | Malek et al. |
| 5,409,818 A | 4/1995 | Davey et al. |
| 5,437,990 A | 8/1995 | Burg et al. |
| 5,514,545 A | 5/1996 | Eberwine et al. |
| 5,716,785 A | 2/1998 | Van Gelder et al. |
| 5,849,547 A | * 12/1998 | Cleuziat et al. .......... 435/91.21 |
| 5,932,451 A | 8/1999 | Wang et al. |
| 5,958,688 A | 9/1999 | Eberwine et al. |
| 6,027,913 A | * 2/2000 | Sommer .................... 435/69.1 |
| 6,090,562 A | 7/2000 | Bridgham et al. |
| 6,090,591 A | 7/2000 | Burg et al. |
| 6,100,043 A | 8/2000 | Bridgham et al. |
| 6,110,711 A | 8/2000 | Serafini et al. |
| 6,114,152 A | 9/2000 | Serafini et al. |
| 6,132,997 A | 10/2000 | Shannon |
| 6,582,938 B1 | * 6/2003 | Su et al. .................... 435/91.2 |

FOREIGN PATENT DOCUMENTS

| EP | 1043405 A2 | 10/2000 |
| WO | WO 99/31277 | 6/1999 |
| WO | WO99/43850 | * 9/1999 |

OTHER PUBLICATIONS

Kwoh et al., Transcription–based amplification system and detection of amplified human immunodeficiency virus type 1 with a bead–based sandwich hybridization format. Proc. Natl. Acad. Sci. USA, vol. 86, pp. 1173–1177, (1989).

* cited by examiner

Primary Examiner—Jeffrey Siew
(74) Attorney, Agent, or Firm—Sandra E. Wells; Philip L. McGarrigle

(57) ABSTRACT

The present invention relates to the amplification of nucleic acids, preferably from mRNA. A primer and promoter are added to a target sequence to be amplified and then the target is amplified in an in vitro transcription reaction and the product of this reaction is used as template for subsequent rounds of amplification.

34 Claims, 3 Drawing Sheets

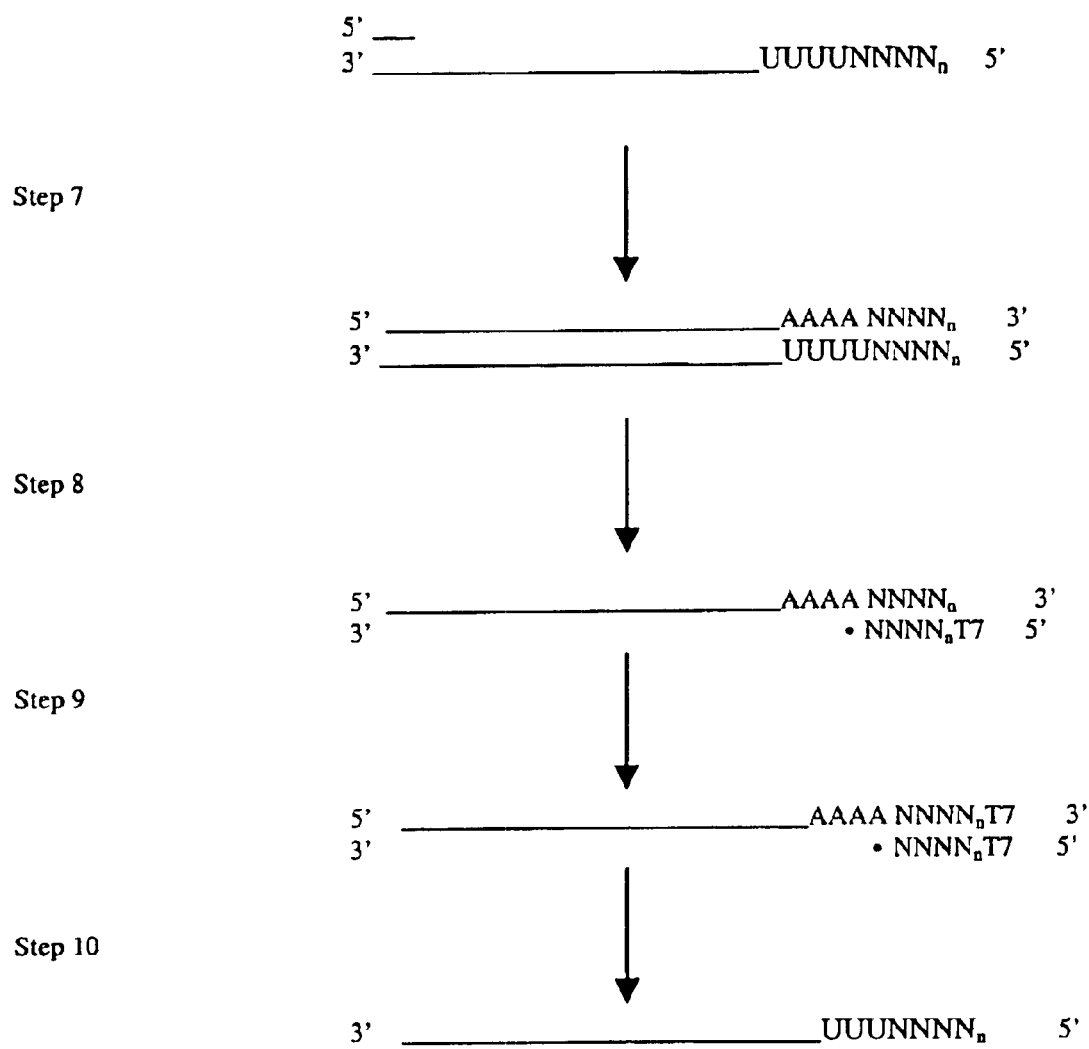

METHODS OF SMALL SAMPLE AMPLIFICATION

RELATED APPLICATIONS

The present application claims the benefit of U.S. Provisional Patent Application Ser. No. 60/172,340 filed Dec. 16, 1999 and is a continuation-in-part of U.S. application Ser. Nos. 09/738,892filed Dec. 18, 2000 and 09/854,317 filed May 11, 2001, now U.S. Pat. No. 6,582,938, the disclosures of which are incorporated herein by reference.

FIELD OF THE INVENTION

The present invention relates generally to the amplification of nucleic acids. More specifically, the present invention facilitates the amplification of mRNA for a variety of end uses.

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle progression, cell differentiation and cell death, are often characterized by the variations in the expression levels of a group of genes.

Gene expression is also associated with pathogenesis. For example, the lack of sufficient expression of functional tumor suppressor genes and/or the over expression of oncogene/protooncogenes could lead to tumorgenesis (Marshall, *Cell*, 64: 313–326 (1991); Weinberg, *Science*, 254: 1138–1146 (1991), incorporated herein by reference for all purposes). Thus, changes in the expression levels of particular genes (e.g. oncogenes or tumor suppressors) serve as signposts for the presence and progression of various diseases.

Highly parallel methods of monitoring the expression of a large number of genes in a biological sample are a valuable research and diagnostics tool. However, the amount of starting material that can be obtained from a given source is often limited and it is useful to amplify genetic material prior to analysis. Methods of amplification that allow analysis of a sample that may be too small for analysis without amplification facilitate the analysis of gene expression in small samples and possibly in a single cell.

SUMMARY OF THE INVENTION

The present invention provides methods for monitoring expression of a plurality of genes in a cell, one or more cells, a small population of cells or a small amount of biological sample. Preferred methods entail amplifying a population of nucleic acids derived from a population of fewer than 1000 cells.

The invention provides methods for the amplification of nucleic acids that may comprise synthesizing double-stranded DNA from a single-stranded DNA population, and producing multiple copies of RNA from the double-stranded DNA. The method further comprises a second round of amplification comprising: synthesizing single stranded DNA from the multiple copies of RNA and producing multiple copies of RNA from the DNA. The second round of amplification may be repeated.

More specifically, in one preferred embodiment (see, FIG. 1), the method comprises contacting a mRNA having a poly dA tail with a primer comprising poly d(T) and a second sequence; generating a first cDNA strand from the mRNA strand by extending the primer by reverse transcriptase and the appropriate nucleotides under the appropriate conditions, which creates a RNA:DNA duplex; digesting the RNA with RNaseH; forming a double stranded DNA; denaturing the double stranded DNA to form a single stranded DNA and adding a promoter to the single stranded DNA, the promoter comprising a complement to the second sequence and a RNA polymerase promoter sufficient to form a functional promoter when the promoter is hybridized to the single stranded DNA; forming a double stranded DNA promoter region by adding the appropriate reagents; and, producing multiple copies of RNA from the DNA strand comprising the promoter, the RNA copies comprising a complement to at least a portion of the second sequence. Preferably, the promoter is blocked from 3' extension.

The method further comprises a second round of amplification (see, FIG. 1, steps 7–10), comprising contacting the multiple RNA copies with random primers; generating a first strand cDNA from the RNA by extending the primers with reverse transcriptase and the appropriate nucleotides under the appropriate conditions, which creates a RNA:DNA duplex; digesting the RNA:DNA duplex with for example, RNaseH, to form a single stranded DNA and adding a primer to the single stranded DNA, the primer comprising a complement to the second sequence and an RNA polymerase promoter sufficient to form a functional promoter when the primer is hybridized to the single stranded DNA, forming a double stranded DNA promoter region by adding the appropriate reagents; and, producing multiple copies of RNA from the DNA strand comprising the promoter. Preferably, the promoter is blocked from 3' extension.

In another embodiment of the invention (see FIG. 2), the method comprises contacting a mRNA having a poly dA tail with a primer comprising poly d(T) and a second sequence that is a promoter; generating a first cDNA strand from the mRNA strand by extending the primer by reverse transcriptase and the appropriate nucleotides under the appropriate conditions, which creates a RNA:DNA duplex; denaturing the RNA:DNA duplex; contacting the resulting single stranded DNA with random primers and extending the primers with DNA polymerase and the appropriate nucleotides under the appropriate conditions; which creates a double stranded DNA with a promoter region; and, producing multiple copies of RNA from the DNA strand comprising the promoter.

The method further comprises a second round of amplification, (see, FIG. 2 steps 5–10 comprising contacting the multiple RNA copies with random primers; generating a first cDNA strand from the RNA by extending the primers with reverse transcriptase and the appropriate nucleotides under the appropriate conditions, which creates a RNA:DNA duplex; denaturing the RNA:DNA duplex to form a single stranded DNA and contacting the single stranded DNA with a primer comprising poly d(T) and a second sequence that is a promoter, forming a double stranded DNA by extending the primer with DNA polymerase and the appropriate nucleotides under the appropriate conditions; forming a double stranded DNA promoter region by adding the appropriate reagents; and, producing multiple copies of RNA from the DNA strand comprising the promoter.

In another embodiment the second round of amplification is repeated at least one time.

Among other factors, the present invention provides new methods for amplification of nucleic acids. The methods are particularly useful for amplification of small samples such as a sample derived from 1000 or fewer cells. Additionally, in one embodiment, the present invention is an amplification method in which a promoter is protected from degradation throughout the method.

The present invention also preferably provides methods, which may further comprise contacting the multiple copies of RNA with a solid support comprising nucleic acid probes, and detecting the presence or absence of hybridization of the RNA to the nucleic acid probes on the solid support. In a preferred embodiment, the solid support, which may comprise nucleic acid probes, can be selected from the group consisting of a nucleic acid probe array, a membrane blot, a microwell, a bead, and a sample tube.

In yet another preferred embodiment, the invention relates to a kit comprising reagents and instructions for the amplification of mRNA. Preferably, the kit includes a reaction vessel containing one or more reagents in concentrated form, where the reagent may be an enzyme or enzyme mixture. The kit also includes a container, instructions for use, a primer which comprises a poly d(T) sequence operably linked to a second sequence, and a primer comprising the second sequence or its equivalent operably linked to a promoter sequence. Preferably, the primer comprising the promoter is blocked from extending in the 3' direction.

In yet another preferred embodiment, the invention relates to a kit comprising reagents and instructions for the amplification of mRNA. Preferably, the kit includes a reaction vessel containing one or more reagents in concentrated form, where the reagent may be an enzyme or enzyme mixture. The kit also includes a container, instructions for use, and a primer which comprises a poly d(T) sequence operably linked to a second sequence comprising a promoter.

DETAILED DESCRIPTION OF THE PREFERRED EMBODIMENTS

General

Figure 1:
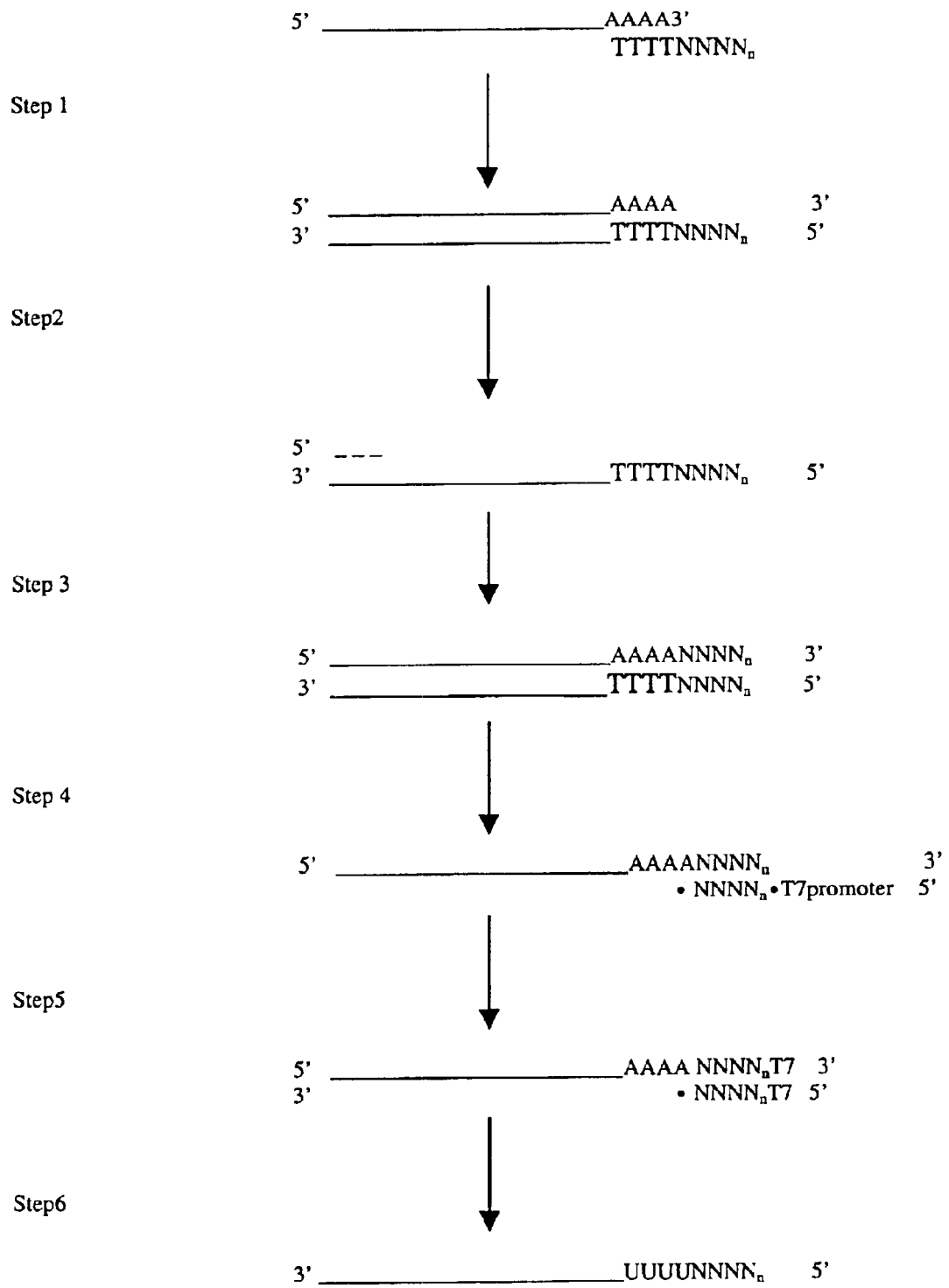
FIG. 1 depicts an aspect of a preferred embodiment of the invention in which a primer is used to create a DNA strand and in a subsequent step a blocked oligonucleotide is used as a template to extend a poly A DNA strand to build a functional T7 promoter. Subsequently, T7 RNA polymerase will use the sense strand as a template to make cRNA resulting in antisense cRNA. Random primers are used to prime synthesis of a cDNA copy of the cRNA and in a subsequent step a blocked oligonucleotide is used as a template to extend a poly A DNA strand to build a functional T7 promoter. Subsequently, T7 RNA polymerase will use the sense strand as a template to make cRNA resulting in antisense RNA.

The present invention relies on many patents, applications and other references for details known to those of the art. Therefore, when a patent, application, or other reference is cited or repeated below, it should be understood that it is incorporated by reference in its entirety for all purposes as well as for the proposition that is recited.

As used in the specification and claims, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques can be found in standard laboratory manuals such as *Genome Analysis: A Laboratory Manual Series* (Vols. I–IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), all of which are herein incorporated in their entirety by reference for all purposes.

Methods and techniques applicable to array synthesis have been described in U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, and 6,090,555, which are all incorporated herein by reference in their entirety for all purposes.

Additionally, gene expression monitoring and sample preparation methods can be shown in U.S. Pat. Nos. 5,800,992, 6,040,138, and 6,013,449.

Definitions

Nucleic acids according to the present invention may include any polymer or oligomer of pyrimidine and purine bases, preferably cytosine, thynine, and uracil, and adenine and guanine, respectively. (See Albert L. Lehninger, *Principles of Biochemistry*, at 793–800 (Worth Pub. 1982)). Indeed, the present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Oligonucleotide and polynucleotide are included in this definition and relate to two or more nucleic acids in a polynucleotide. (See U.S. Pat. No. 6,156,501 which is hereby incorporated by reference in its entirety.)

Array: An array comprises a support, preferably solid, with nucleic acid probes attached to said support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767–777 (1991), each of which is incorporated by reference in its entirety for all purposes. These arrays may generally be produced using mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostics or can be an all-inclusive device; e.g., U.S. Pat. Nos. 5,856,174 and 5,922,591 incorporated in their entirety by reference for all purposes. (See also U.S. patent application Ser. No. 09/545,207 for additional information concerning arrays, their manufacture, and their characteristics.) It is hereby incorporated by reference in its entirety for all purposes.

Preferred arrays are commercially available from Affymetrix under the brand name GeneChip® and are directed to a variety of purposes, including gene expression monitoring for a variety of eukaryotic and prokaryotic species. (See Affymetrix Inc., Santa Clara and their website at affymetrix.com.)

The Process

In general, the presently preferred invention enables a user to amplify mRNA (a target sequence) for gene expression monitoring experiments. Although one of skill in the art will recognize that other uses may be made of the amplified nucleic acid. In one embodiment of the current invention (See FIG. 1.) mRNA is contacted with a poly d(T) primer preferably having a unique sequence attached to the poly d(T). The unique sequence can be one that has no function and can operate as a 'tag' or 'adaptor', but it must be one that will not cross hybridize to other nucleic acids that can be present.

The primer is extended using the mRNA as template to synthesize the first strand cDNA (step 1), the mRNA strand is preferably denatured (step 2), and then a second DNA strand is synthesized using conventional methods (step 3). The DNA strands are then separated (step 4) and a second oligonucleotide sequence is added, which contains the unique sequence that was added on with the poly d(T) and a functional promoter. The portion of the second added oligonucleotide sequence that is single stranded is filled in (made double stranded) so that there is a functional promoter operably linked to the target sequence (step 5). (For additional information on amplification with a blocked promoter primer see, U.S. application Ser. No. 09/854,317, which is herein incorporated by reference in its entirety for all purposes.) Thereafter, the appropriate reagents are added to transcribe the target portion in an in vitro translation (IVT) reaction (step 6). Preferably, the second oligonucleotide sequence is constructed so that it does not serve as a primer for extension of a sequence that is complementary to the target sequence, i.e. it is blocked. Blocking the end of a nucleic acid is known to one of skill in the art.

For the second round of amplification, (see FIG. 1, steps 7–10) random primers are added and a second, single stranded DNA is synthesized using the RNA product of the first round as a template (step 7). The RNA-DNA duplex is denatured (step 8) and a third oligonucleotide sequence is added, which may comprise at least part of the unique sequence that was added on with the poly d(T) and a functional promoter. The portion of the third sequence that is single stranded is filled in (made double stranded) so that there is a functional promoter operably linked to the target sequence (step 9). Thereafter, the appropriate reagents are added to transcribe the target portion in an IVT reaction (step 10). The third oligonucleotide sequence may be constructed so that it does not serve as a primer for extension of a sequence that is complementary to the target sequence, i.e. it is blocked.

Also, in one alternative embodiment, the poly d(T) of the first oligonucleotide sequence may be at least partially replaced by U. After second cDNA synthesis, the U can be digested by uracil DNA glycosidase, to allow for efficient annealing of the promoter containing oligonucleotide to the cDNA.

Figure 2:
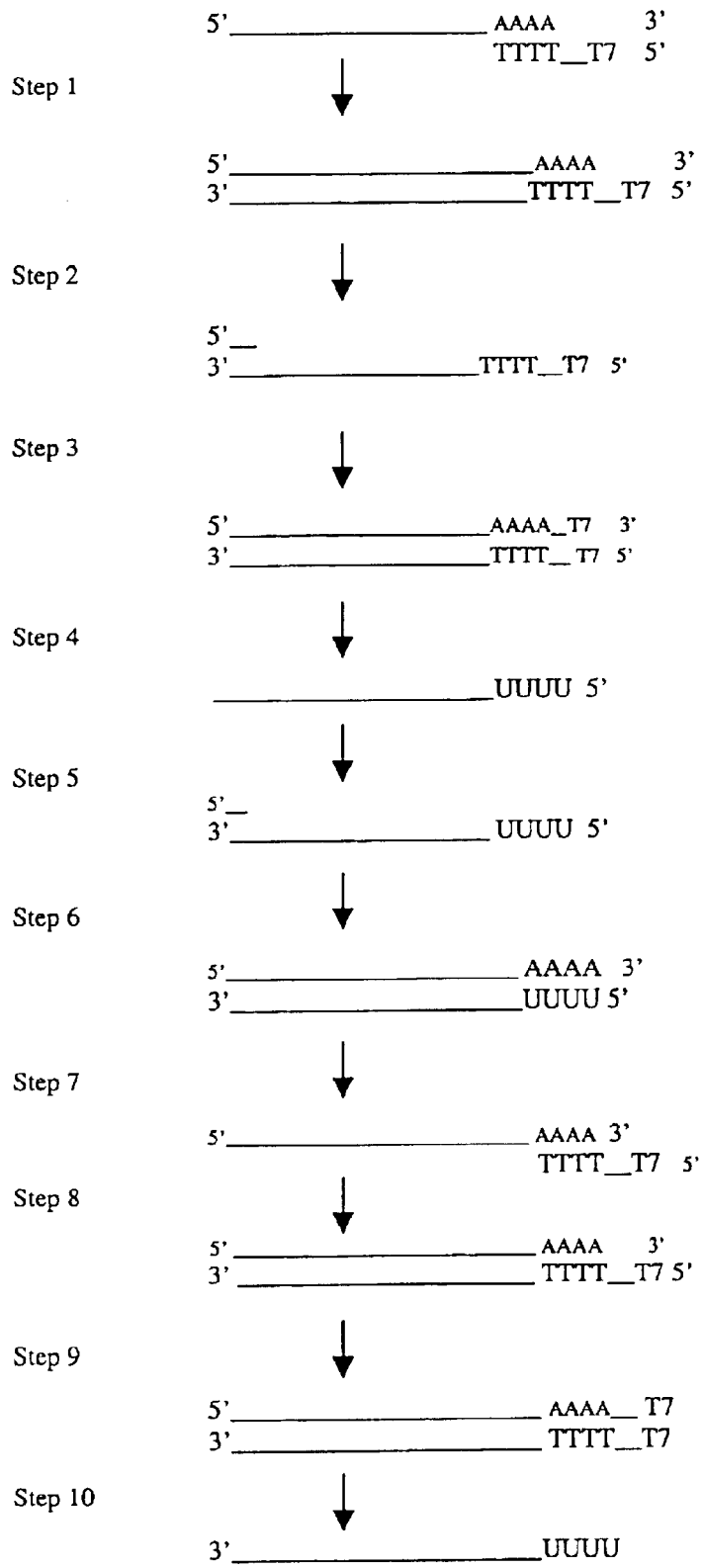
FIG. 2 depicts an aspect of a preferred embodiment of the invention in which a primer comprising poly d(T) and a promoter sequence is used to create a DNA strand and in a subsequent step random primers are used to create a double stranded DNA with a functional T7 promoter. Subsequently, T7 RNA polymerase will use the sense strand as a template to make cRNA resulting in antisense cRNA. Random primets are used to prime synthesis of a cDNA copy of the cRNA and in a subsequent step a primer comprising poly d(T) and a promoter sequence is used as a primer to make a double stranded DNA and as a template to extend a poly A DNA strand to build a functional T7 promoter. Subsequently, T7 RNA polymerase will use the sense strand as a template to make cRNA resulting in antisense RNA.

In a second embodiment (see FIG. 2) mRNA is contacted with a poly d(T) primer-attached to a promoter sequence. A first DNA strand is synthesized (step 1), the mRNA strand is preferably denatured, random primers are added (step 2) and a second DNA strand is synthesized using DNA polymerase, forming an operable promoter (step 3). Thereafter, the appropriate reagents are added to transcribe the target portion in an IVT reaction to synthesize antisense RNA (step 4).

For the second round of amplification, (see FIG. 2, steps 5–10) random primers are added (step 5) and a second, single stranded DNA is synthesized with reverse transcriptase using the RNA as a template (step 6). The RNA-DNA duplex is denatured and the DNA is contacted with an oligonucleotide sequence, which comprises poly d(T) and a functional promoter (step 7). The oligonucleotide is extended to make a second strand DNA (step 8) and the first strand DNA is filled in (made double stranded) so that there is a functional promoter operably linked to the target sequence (step 9). Thereafter, the appropriate reagents are added to transcribe the target portion in an IVT reaction (step 10). Alternatively, the oligonucleotide sequence may be constructed so that it does not serve as a primer for extension of a sequence that is complementary to the target sequence, i.e. it is blocked.

More specifically, one presently preferred embodiment of the invention (see, FIG. 1) is as follows: PolyA+ containing mRNA or total RNA is annealed with the single-stranded oligo d(T)-tailed primer, such as $T_{24}N_{18}$ or $T_xN_y$, creating a primer-template mixture. First strand cDNA synthesis is accomplished by combining the first strand cDNA reagent mix (Superscript II buffer, DTT, and dNTPs) and enzyme mix (SuperScript, ThermoScriptase, and RNAout) with the primer-template mixture and incubating at the appropriate time and temperature. A second strand cDNA is then formed by mixing the first strand cDNA reaction with second strand reagent mix, containing secondary cDNA mix (DEPC-$H_2O$, Tris-HCl (pH7.0), $MgCl_2$, $(NH_4)SO_4$, beta-$NAD^+$, and dNTPs) and CDNA enzyme mix (Vent DNA polyrnerase, Amplitaq DNA polymerase, *E. coli* ligase, *E. coli* RNase H, and *E. coli* DNA polymerase I), followed by incubation at the appropriate times and temperatures. The resultant DNA is then denatured and mixed with a primer that contains a promoter, "promoter primer", which is an extension of Nx. (See, e.g., FIG. 1 for details), to create a promoter primer-template mixture. Formation of a DNA strand that can serve as a template for an IVT reaction is then accomplished by combining the promoter primer-template mixture with Klenow fragment of *E. coli* DNA polymerase I and incubating at the appropriate times and temperatures (only the promoter region needs to be double stranded). Preferably, the promoter primer is engineered to ensure that extension in the 3' direction is blocked. The resulting double-stranded (ds) cDNA contains a functional T7 RNA polymerase promoter, which is utilized for transcription. In vitro transcription (IVT) is performed by combining the (ds) cDNA with IVT reagent (buffer, NTP, DTT, RNase inhibitor, and T7 RNA polymerase), yielding amplified, antisense RNA.

The RNA product of the first round of amplification is then used as template for a second round of amplification. Random primers are hybridized to the RNA creating a primer-template mixture. First strand cDNA synthesis is accomplished by combining the first strand cDNA reagent mix (Superscript II buffer, DTT, and dNTPs) and enzyme mix (SuperScript, ThernoScriptase, and RNAout) with the primer-template mixture and incubating at the appropriate time and temperature. The resultant RNA:DNA duplex is then denatured and mixed with a primer that contains a promoter, "promoter primer", which is an extension of Nx. (See, e.g., FIG. 1 for details), to create a promoter primer-template mixture. Formation of a DNA strand that can serve as a template for an IVT reaction is then accomplished by combining the promoter primer-template mixture with Klenow fragment of *E. coli* DNA polymerase I and incubating at the appropriate times and temperatures (only the promoter region needs to be double stranded). Preferably, the promoter primer is engineered to ensure that extension in the 3' direction is blocked. The resulting double-stranded (ds) cDNA contains a functional T7 RNA polymerase promoter, which is utilized for transcription. IVT is performed by combining the (ds) cDNA with IVT reagent (buffer, NTP, DTT, RNase inhibitor, and T7 RNA polymerase), yielding amplified, antisense RNA. The second round of amplification may be repeated one or more times.

In a second embodiment (see, FIG. 2) the invention is as follows: PolyA+ containing mRNA or total RNA is annealed with the single-stranded oligo d(T)-tailed primer with a promoter sequence, such as $T_xN_x$, where $N_x$ comprises an RNA polymerase promoter sequence such as the T7 promoter sequence, creating a primer-template mixture. First strand cDNA synthesis is accomplished by combining the first strand cDNA reagent mix (Superscript II buffer, DTT, and dNTPs) and enzyme mix (SuperScript II, ThermoScriptase, and RNAout) with the primer-template mixture and incubating at the appropriate time and temperature. A second strand cDNA is then formed by mixing the first strand cDNA reaction with random primers and second strand reagent mix, containing secondary cDNA mix (DEPC-$H_2O$, Tris-HCl (pH7.0), $MgCl_2$, $(NH_4)SO_4$, beta-$NAD^+$, and dNTPs) and cDNA enzyme mix (Vent DNA polymerase, Amplitaq DNA polymerase, *E. coli* ligase, *E. coli* RNase H, and *E. coli* DNA polyrnerase I), followed by incubation at the appropriate times and temperatures. The resulting double-stranded (ds) cDNA contains a functional T7 RNA polymerase promoter, which is utilized for transcription. In vitro transcription (IVT) is performed by combining the (ds) cDNA with IVT reagent (buffer, NTP, DTT, RNase inhibitor, and T7 RNA polymerase), yielding amplified, antisense RNA.

The RNA product of the first round of amplification is then used as template for a second round of amplification. Random primers are hybridized to the RNA creating a primer-template mixture. First strand cDNA synthesis is accomplished by combining the first strand cDNA reagent mix (Superscript II buffer, DTT, and dNTPs) and enzyme mix (SuperScript, ThermoScriptase, and RNAout) with the primer-template mixture and incubating at the appropriate time and temperature. The resultant RNA:DNA duplex is then denatured and mixed with an oligo d(T)-tailed primer with a promoter sequence, such as $T_xN_x$, where $N_x$ comprises an RNA polymerase promoter sequence. Formation of a DNA strand that can serve as a template for an IVT reaction is then accomplished by combining the promoter primer-template mixture with Klenow fragment of *E. coli* DNA polymerase I and T4 DNA polymerase and incubating at the appropriate times and temperatures (only the promoter region needs to be double stranded). The resulting double-stranded (ds) cDNA contains a functional T7 RNA polymerase promoter, which is utilized for transcription. In vitro transcription (IVT) is performed by combining the (ds) cDNA with IVT reagent (buffer, NTP, DTT, RNase inhibitor, and T7 RNA polymerase), yielding amplified, antisense RNA. The second round of amplification may be repeated one or more times. (See also U.S. application Ser. No. 09/285,658.)

The present invention can be combined with other processes to eliminate the need for multiple steps and varying reaction conditions and their associated problems. (See, e.g., PCT/US00/20563, which is hereby incorporated by reference in its entirety.) In preferred embodiments of the present invention, at least three otherwise separate enzymatic reactions can occur consecutively in one phase (ie., without organic extraction and precipitation), more preferably in the same reaction vessel. Preferably, cDNA synthesis according to the present invention may occur in a modified low salt buffer. In addition, the invention may involve an enzyme mix, which may include a thermal stable DNA polymerase and reverse transcriptase for the production of cDNA, and RNA polymerase for RNA transcription. The enzyme activity may be inactivated at the appropriate step with either heat or chemical treatment (for example, adjusting the salt concentration) or by the addition of an antibody specific to the enzyme.

Those skilled in the art will recognize that the products and methods embodied in the present invention may be applied to a variety of systems, including commercially available gene expression monitoring systems involving nucleic acid probe arrays, membrane blots, microwells, beads, and sample tubes, constructed with various materials using various methods known in the art. Accordingly, the present invention is not limited to any particular environment, and the following description of specific embodiments of the present invention are for illustrative purposes only.

In a preferred embodiment, the present invention can involve the amplification of nucleic acids, such as mRNA. However, other nucleic acids may be amplified such as by synthesizing double-stranded DNA from a single-stranded DNA population, and producing multiple copies of RNA from the double-stranded DNA, where the synthesizing and producing occur in reaction vessels, preferably in the same reaction vessel.

The reaction vessel according to the present invention may include a membrane, filter, microscope slide, microwell, sample tube, array, or the like. (See International Patent applications No. PCT/US95/07377 and PCT/US96/11147, which are expressly incorporated herein by reference.) The reaction vessel may be made of various materials, including polystyrene, polycarbonate, plastics, glass, ceramic, stainless steel, or the like. The reaction vessel may preferably have a rigid or semi-rigid surface, and may preferably be conical (e.g., sample tube) or substantially planar (e.g., flat surface) with appropriate wells, raised regions, etched trenches, or the like. The reaction vessel may also include a gel or matrix in which nucleic acids may be embedded. (See A. Mirzabekov et al., *Anal. Biochem.* 259 (1):34–41 (1998), which is expressly incorporated herein by reference.)

The single-stranded or double-stranded DNA populations according to the present invention may refer to any mixture of two or more distinct species of single-stranded mRNA, DNA or double-stranded DNA, which may include DNA representing genomic DNA, genes, gene fragments, oligonucleotides, polynucleotides, nucleic acids, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a mRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like.

Where the nucleic acid sample contains RNA, the RNA may be total RNA, poly(A)$^+$RNA, mRNA, rRNA, or tRNA, and may be isolated according to methods known in the art. (See, e.g., T. Maniatis et al., *Molecular Cloning: A Laboratory Manual*, 188–209 (Cold Spring Harbor Lab., Cold Spring Harbor, N.Y. 1982, which is expressly incorporated herein by reference.) The RNA may be heterogeneous, referring to any mixture of two or more distinct species of RNA. The species may be distinct based on any chemical or biological differences, including differences in base composition, length, or conformation. The RNA may contain full length mRNAs or mRNA fragments (i.e., less than full length) resulting from in vivo, in situ, or in vitro transcriptional events involving corresponding genes, gene fragments, or other DNA templates. In a preferred embodiment, the mRNA population of the present invention may contain single-stranded poly(A)+RNA, which may be obtained from an RNA mixture (e.g., a whole cell RNA preparation), for example, by affinity chromatography purification through an oligo-dT cellulose column.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993), all of which are incorporated herein by reference in their entireties for all purposes.

In a preferred embodiment, the total RNA is isolated from a given sample using, for example, an acid guanidinium-phenol-chloroform extraction method and polyA$^+$mRNA is isolated by oligo dT column chromatography or by using (dT)n magnetic beads. (See e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987)). (See also PCT/US99/25200 for complexity management and other sample preparation techniques, which is hereby incorporated by reference in its entirety for all purposes.) Where the single-stranded DNA population of the present invention is cDNA produced from a mRNA population, it may be produced according to methods known in the art. (See, e.g, Maniatis et al., supra, at 213–46.) In a preferred embodiment, a sample population of single-stranded poly(A)+RNA may be used to produce corresponding cDNA in the presence of reverse transcriptase, oligo-dT primer(s) and dNTPs. Reverse transcriptase may be any enzyme that is capable of synthesizing a corresponding cDNA from an RNA template in the presence of the appropriate primers and nucleoside triphosphates. In a preferred embodiment, the reverse transcriptase may be from avian myeloblastosis virus (AMV), Moloney murine leukemia virus (MMuLV) or Rous Sarcoma Virus (RSV), for example, and may be a thermal stable enzyme (e.g., rTth DNA polymerase available from PE Applied Biosystems, Foster City, Calif.).

In a preferred embodiment of the present invention, the single-stranded cDNA produced using a mRNA population as template may be separated from any resulting RNA templates by heat or enzyme treatment (e.g., RNase H). In a preferred embodiment, terminal transferase may be used to add poly(A) or poly(G) sequences to the 3'-termini of the single-stranded DNA. The double-stranded DNA of the present invention may be synthesized from the heterogeneous single-stranded DNA. An oligonucleotide primer may be applied to the poly(A), poly(G), poly(C) or poly (T) tailed heterogeneous single-stranded DNA. The oligonucleotide primer preferably includes a poly(T) or poly(C) region complementary to the poly(A) or poly(G) tail attached to the single-stranded DNA. In a preferred embodiment, amplification is accomplished through the use of two sequences; the first used for cDNA synthesis and the second used for formation of a DNA strand that can serve as a template for an IVT reaction. In a further preferred embodiment, the primer that comprises the promoter includes a full or partial promoter consensus sequence capable of facilitating transcription by the RNA polymerase used, for example, the DNA-directed RNA polymerases derived from bacteriophage T7, T3 or SP6.

Any of the preferred oligonucleotides may be synthesized, for example, using a PCR-MATE Model 391

DNA synthesizer (Applied Biosystems) and purified by high-performance liquid chromatography before use. Oligonucleotides of sufficient length, quality, sequence and base composition are also available from a large number of commercial vendors, including Genset, Operon, MWG, Research Genetics, and Life Technologies Inc. (LTI). Reverse transcriptase (e.g., either derived from AMV or MuLV) is available from a large number of commercial sources including Invitrogenn/LTI, Amersham Phamacia Biotech (APB)/USB, Qiagen, and others. Other enzymes required or desired are also available from these vendors among others, such as Promega, and Epicentre. Nucleotides such as dNTPs, unique nucleotide sequences, and β-NAD are available from a variety of commercial sources such as APB, Roche Biochemicals, Sigma Chemicals. Buffers, salts and cofactors required or desired for these reactions can usually be purchased from the vendor that supplies a respective enzyme or assembled from materials commonly available, e.g., from Sigma Chemical.

In a preferred embodiment of the present invention, the ends of the double-stranded DNA may be blunted. T4 DNA polymerase or *E. coli* DNA polymerase I (Klenow fragment), for example, may be used preferably to produce blunt ends in the presence of the appropriate dNTPs. Also, in many of the preferred embodiments the promoter containing primer is preferably blocked from extension using methods that are conventional in the art. For example, they can be blocked at the 3' end by a phosphate, a thiol, an amino group or a dideoxy base. Preferably, they can be blocked using a phosphate group. Blocked oligonucleotides can be purchased directly from commercial vendors such as those listed above.

Multiple copies of RNA according to the present invention may be obtained by in vitro transcription from the DNA preferably using T7 RNA polymerase in the presence of the appropriate nucleoside triphosphates.

In a preferred embodiment of the present invention, the multiple copies of RNA may be labeled by the incorporation of biotinylated, fluorescently labeled or radiolabeled CTP or UTP during the RNA synthesis. (See U.S. Pat. Nos. 5,800, 992, 6,040,138 and International Patent Application PCT/US96/14839, which is expressly incorporated herein by reference. Alternatively, labeling of the multiple copies of RNA may occur following the RNA synthesis via the attachment of a detectable label in the presence of terminal transferase. In a preferred embodiment of the present invention, the detectable label may be radioactive, fluorometric, enzymatic, or colorimetric, or a substrate for detection (e.g., biotin). Other detection methods, involving characteristics such as scattering, IR, polarization, mass, and charge changes, may also be within the scope of the present invention.

In a preferred embodiment, the amplified DNA or RNA of the present invention may be analyzed with a gene expression monitoring system. Several such systems are known. (See, e.g., U.S. Pat. No. 5,677,195; Wodicka et al., *Nature Biotechnology* 15:1359–1367 (1997); Lockhart et al., *Nature Biotechnology* 14:1675–1680 (1996), which are expressly incorporated herein by reference.) A preferred gene expression monitoring system according to the present invention may be a nucleic acid probe array, such as the GeneChip® nucleic acid probe array (Affyrnetrix, Santa Clara, Calif.). (See, U.S. Pat. Nos. 5,744,305, 5,445,934, 5,800,992, 6,040, 193 and International Patent applications PCT/US95/07377, PCT/US96/14839, and PCT/US96/14839, which are expressly incorporated herein by reference. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, gel, nylon, polystyrene, polycarbonate, plastics, glass, ceramic, stainless steel, or the like including any other support cited in 5,744,305 or 6,040,193. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded. The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). See U.S. Pat. Nos. 5,770,722, 5,744,305, 5,677,195 5,445,934, and 6,040, 193 which are incorporated here in their entirety by reference. (See also Examples, infra.) The gene expression monitoring system may also comprise nucleic acid probes in solution.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. (See U.S. Pat. Nos. 5,800, 922 and 6,040,138.) In a preferred embodiment, the proportional amplification methods of the present invention can provide reproducible results (i.e., within statistically significant margins of error or degrees of confidence) sufficient to facilitate the measurement of quantitative as well as qualitative differences in the tested samples. The proportional amplification methods of the present invention may also facilitate the identification of single nucleotide polymorphisms (SNPs) (i.e., point mutations that can serve, for example, as markers in the study of genetically inherited diseases) and other genotyping methods from limited sources. (See e.g., Collins et al., 282 *Science* 682 (1998), which is expressly incorporated herein by reference;) The mapping of SNPs can occur by any of various methods known in the art, one such method being described in U.S. Pat. No. 5,679,524, which is hereby incorporated by reference.

The RNA, single-stranded DNA, or double-stranded DNA population of the present invention may be obtained or derived from any tissue or cell source. Indeed, the nucleic acid sought to be amplified may be obtained from any biological or environmental source, including plant, virion, bacteria, fungi, or algae, from any sample, including body fluid or soil. In one embodiment, eukaryotic tissue is preferred, and in another, mammalian tissue is preferred, and in yet another, human tissue is preferred. The tissue or cell source may include a tissue biopsy sample, a cell sorted population, cell culture, or a single cell. In a preferred embodiment, the tissue source may include brain, liver, heart, kidney, lung, spleen, retina, bone, lymph node, endocrine gland, reproductive organ, blood, nerve, vascular tissue, and olfactory epithelium. In yet another preferred embodiment, the tissue or cell source may be embryonic or tumorigenic.

Tumorigenic tissue according to the present invention may include tissue associated with malignant and preneoplastic conditions, not limited to the following: acute lymphocytic leukemia, acute myelocytic leukemia, myeloblastic leukemia, promyelocytic leukemia, myelomonocytic leukemia, monocytic leukemia, erythroleukemia, chronic myelocytic (granulocytic) leukemia, chronic lymphocytic leukemia, polycythernia vera, lymphoma, Hodgkin's disease, non-Hodgkin's disease, multiple myeloma, Waldenstrom's macroglobulinemia, heavy chain disease, solid tumors, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. (See Fishman et al., *Medicine,* 2d Ed. (J. B. Lippincott Co., Philadelphia, Pa. 1985), which is expressly incorporated herein by reference.)

In yet another preferred embodiment of the present invention, a nucleic acid detection system, the amplified DNA or RNA, or fragments thereof, may be immobilized directly or indirectly to a solid support or substrate by methods known in the art (e.g., by chemical or photoreactive interaction, or a combination thereof). (See U.S. Pat. Nos. 5,800,992, 6,040,138 and 6,040,193.) The resulting immobilized nucleic acid may be used as probes to detect nucleic acids in a sample population that can hybridize under desired stringency conditions. Such nucleic acids may include DNA contained in the clones and vectors of cDNA libraries.

The materials for use in the present invention are ideally suited for the preparation of a kit suitable for the amplification of nucleic acids. Such a kit may comprise reaction vessels, each with one or more of the various reagents, preferably by in concentrated form, utilized in the methods. The reagents may comprise, but are not limited to the following: low modified salt buffer, appropriate nucleotide triphosphates (e.g. dATP, dCTP, dGTP, dTTP; or rATP, rCTP, rGTP, and UTP) reverse transcriptase, RNase H, thermal stable DNA polymerase, RNA polymerase, DNA polymerase, ligase. RNase inhibitors and the appropriate primer complexes. In addition, the reaction vessels in the kit may comprise 0.2–1.0 ml tubes capable of fitting a standard thermocycler, which may be available singly, in strips of 8, 12, 24, 48, or 96 well plates depending on the quantity of reactions desired. Hence, the amplification of nucleic acids may be automated, e.g., performed in a PCR theromcycler. The thermocyclers may include, but are not limited to the following: Perkin Elmer 9600, MJ Research PTC 200, Techne Gene E, Erichrom, and Whatman Biometra T1 Thermocycler.

Also, the automated machine of the present invention may include an integrated reaction device and a robotic delivery system. In such cases, part of all of the operation steps may automatically be done in an automated cartridge. (See U.S. Pat. Nos. 5,856,174, 5,922,591, and 6,043,080.)

Without further elaboration, one skilled in the art with the preceding description can utilize the present invention to its fullest extent. The following examples are illustrative only, and not intended to limit the remainder of the disclosure in any way.

EXAMPLE ONE

Step 1: Primer-template annealing and first strand cDNA synthesis. Obtain the HPLC purified Primer from a −20° C. storage stock, prepare it in a 100 $\mu$M solution with TE (10 mM Tris-HCl (pH 8.0) and 1 mM EDTA (pH 8.0)) and dilute 1:1 with glycerol (for a final concentration of 50 $\mu$M in 50% glycerol and 50% TE). Where the desired nucleic acid sample is poly(A)+RNA, use a $T_{20}$ primer attached to a unique nucleic acid sequence. In such case, mix an RNA sample (0.1 to 1 ng mRNA or 1–100 ng total RNA suspended in 5.5 $\mu$l or less) with 0.5 to 100 pmol primer to give a final volume of 6 $\mu$l. Incubate the mixture at 70° C. for 3 minutes, then cool to 4° C.

First strand cDNA synthesis. To the 6 $\mu$l Primer-template mixture, add 3 $\mu$l of RT buffer and 1 $\mu$l of RT enzyme mixture. Incubate this 10 $\mu$l reaction mixture at 37° C. for 20 minutes, 65° C. for 20 minutes, then cool to 4° C. or on ice.

Prepare the RT buffer in 150 $\mu$l aliquots for 50 reactions by combining 100 $\mu$l 5×1° cDNA buffer (shipped with Superscript II) 25 $\mu$l DTT (0.1 M), and 25 $\mu$l dNTP (10 mM).

Prepare the RT enzyme mixture by combining SuperScript (200 U/$\mu$l), ThermoScriptase (15 U/$\mu$l), and RNAout (40 U/$\mu$l), all of which are available from Life Technologies, Inc., Gaithersburg, Md., in a 1:1:1 mixture.

Steps 2 and 3: RNA digestion and second strand cDNA synthesis. Mix the 10 $\mu$l first strand cDNA reaction mixture with 9 $\mu$l secondary cDNA buffer and 1 $\mu$l secondary enzyme mix and incubate at 16° C. for 105 minutes, 75° C. for 15 minutes, then cool to 4° C. or on ice.

Prepare the secondary cDNA mix in 450 $\mu$l aliquots for 50 reactions by combining 245 $\mu$l RNase-free $H_2O$, 40 $\mu$l of 1 M Tris HCl (pH 7.0), 35 $\mu$l of 0.1 M $MgCl_2$, 100 $\mu$l of 0.1 M $(NH_4)_2SO_4$, 15 $\mu$l of 10 mM beta-$NAD^+$, and 15 $\mu$l of 10 mM dNTP.

Prepare the cDNA enzyme mix in 50 $\mu$l aliquots for 50 reactions by combining, in a screw-capped tube cooled to −20° C., 2 $\mu$l of Vent DNA polymerase (2 U/$\mu$l) (NEB, Inc., Beverly, Mass.), 5 $\mu$l of AmpliTaq DNA polymerase (5 U/$\mu$l) (PE Biosystems, Foster City, Calif.), 5 $\mu$l of *E. coli* ligase (10 U/$\mu$l) (available from, for example, NEB, Inc., Beverly, Mass.), 6 $\mu$l of *E. coli* RNase H (2 U/$\mu$l) (available from, for example, Promega, Inc., Madison, Wis.), and 25 $\mu$l of *E. coli* DNA polymerase I (10 U/$\mu$l) (available from, for example, NEB, Inc., Beverly, Mass.). Adjust the total volume of this mixture to 50 $\mu$l with 7 $\mu$l of 50% cold glycerol, followed by a brief and gentle mix and quick spin before storage at −20° C.

Steps 4 and 5: Formation of a DNA strand for an IVT reaction. Mix the 20 $\mu$l second strand cDNA reaction with 1 $\mu$l of a primer that comprises a promoter and having an overlap with the primer used above so that it can hybridize. Heat this mixture to 95° C. for 5 minutes then cool to 4° C. or on ice. Mix the 21 $\mu$l reaction mixture with 0.5 $\mu$l (2.5 units) Klenow fragment of DNA polymerase I (available from, for example, NEB, Inc., Beverly, Mass.), incubate at 37° C. for 30 minutes, 72° C. for 15 minutes, then cool to 4° C. or on ice.

De-salting(optional step) Pass each reaction through a S-300 column (available from Amersham Pharmacia Biotech ) spun at 1000×g for 1 minute.

cRNA Synthesis

Step 6: In vitro transcription. To achieve maximal amplification, combine the 22 µl total volume of double-stranded cDNA with 18 µl of IVT reagent, which may contain Buffer, NTP mix, DTT, and enzyme mix (all reagents from MEGAscript T7 kit available from Ambion, Inc., Austin, Tex.).

Incubate the 40 µl total volume mixture at 37° C. for 4–6 hours, the incubation can be 30 minutes to many hours.

The sample may be concentrated before the second round.

Second Round of Amplification cDNA Synthesis

Step 7: Primer template annealing and first strand cDNA synthesis. Mix the RNA with 0.5 to 1 ug of random hexamers and incubate at 70° C. for 3 minutes, then cool to 4° C.

Add RT buffer and RT enzyme mixture to the primer-template mixture, and incubate at 37° C. for 60 minutes, then cool to 4° C. or on ice.

Step 8: Heat denature and anneal primer. Mix this reaction with 5 to 150 pmol of a primer that comprises a promoter and having an overlap with the 3' end of the RNA so that it can hybridize. Heat this mixture to 95° C. for 5 minutes then cool to 4° C. or on ice.

Step 9: Formation of a DNA strand for an IVT reaction. Mix the reaction mixture with 0.5 µl (2.5 units) Klenow fragment of DNA polymerase I (available from, for example, NEB, Inc., Beverly, Mass.), incubate at 37° C. for 30 minutes, 72° C. for 15 minutes, then cool to 4° C. or on ice.

cRNA Synthesis

Step 10: In vitro transcription. To achieve maximal amplification, combine the 22 µl total volume of DNA with 18 µl of IVT reagent, which may contain 4 µl of Enzo Buffer, 4 µl of NTP mix, 4 µl DTT, 4 µl RNase Inhibitor and 2 µl enzyme (all reagents from Enzo BioArray High yield RNA Transcript Labeling kit distributed by Affymetrix for Enzo Diagnostic Inc. Farmingdale, N.Y.).

Incubate the 40 µl total volume mixture at 37° C. for 4–6 hours, the incubation can be 30 minutes to many hours.

The resulting samples may be subjected to another round of amplification, stored at −20° C., or analyzed.

Analysis may occur through the resolution of a 0.5 µl or 1 µl sample on a 1% agarose gel. Purification or quantification of the nucleic acid sample may occur by any one of the methods known in the art.

EXAMPLE TWO

First Round Amplification

First Strand cDNA Synthesis

Use 0.2 µl PCR tube for the following reactions and run the reactions in a PCR machine. Incubate 1 µl total RNA, (1 ng/µl, freshly diluted) with 1 µl T7-(dT)$_{24}$ primer at 70° C. for 6 min then put on ice for 2 min. Prepare RT premix 1 by mixing 2 µl DEPC water, 4 µl 5×first strand buffer, 2 µl 0.1 M DTT, 1 µl 10 mM dNTP mix, 1 µl Rnase inhibitor (40 units/µl) and 2 µl Superscript II (200 units/µl). Add 3 µl of the RT premix to the denatured RNA and primer. The total volume is 5 µl. Mix and spin down, then incubate at 42° C. for 1 hour.

Second Strand cDNA Synthesis

Prepare SS Premix 1 by mixing 91 µl DEPC water, 30 µl 5×Second Strand Buffer, 3 µl 10 mM dNTP Mix, 1 µl E. coli DNA ligase (10 units/µl), 4 µl E. coli DNA polymerase (10 units/µl) and 1 µl RNase H (2 units/µl). Spin down the first strand reaction and put on ice, then add 32.5 µl of the SS Premix 1 to the first strand reaction. Mix and spin down, then incubate at 16° C. for 2 hours. Add 1 µl T4 DNA polymerase (5 units/µl) to the above reaction and incubate at 16° C. for 15 min.

Clean up the double stranded cDNA by ethanol precipitation.

Antisense RNA Synthesis

Add 4 µl DEPC water, 4 µl pre-mixed 10×NTP (75 mM each NTP), 1 µl 10×reaction buffer and 1 µl enzyme mix to the dried sample from above (all reagents available in MEGAscript T7 Kit, available from Ambion, Inc., Austin Tex.). Mix and incubate at 37° C. for 4 hours.

Use Rneasey Mini Kit from Qiagen, Valencia, Calif. according to the Rneasey mini Protocol for RNA Cleanup from the Qiagen handbook to clean up the cRNA. Add 90 µl of RNase-free water to the reaction from step 4 and elute from the column in 50 µl RNase-free water. Concentrate the volume to 4 µl.

Second Round of Amplification

First Strand cDNA Synthesis

To the 4 µl of cRNA from the first round of amplification, add 1 µl random primers (0.5 µg/µl) and incubate at 70° C. for 10 min then put on ice for 2 min. Prepare RT premix 2 by mixing 1 µl DEPC water, 4 µl 5×first strand buffer, 2 µl 0.1 M DTT, 1 µl 10 mM dNTP mix, 1 µl RNase inhibitor (40 units/µl) and 1 µl Superscript II (200 units/µl). Add 5 µl of the RT Premix 2 to the denatured RNA and primer. Mix and spin, then incubate at 42° C. for 1 hour. Add 1 µl RNase H (2 units/µl) and incubate for 20 min at 37° C., then heat at 95° C. for 5 min and chill on ice.

Second Strand cDNA Synthesis

Spin down the first strand reaction then add 1 µl T7-(dT)$_{24}$ primer (100 ng/µl) and incubate at 70° C. for 6 min then put on ice. Prepare SS premix 2 by mixing 91 µl DEPC water, 30 µl 5×Second Strand Buffer, 3 µl 10 mM dNTP mix, and 4 µl E. coli DNA polymerase (10 units/µl). Add 64 µl SS Premix 2 to the above reaction, mix and spine down then incubate at 16° C. for 2 hours. Then add 2 µl T4 DNA polyrnerase (5 units/µl) and incubate at 16° C. for 15 min.

Clean up the double stranded cDNA by ethanol precipitation.

Biotin Labeled Anitsense RNA Synthesis

To the dried double stranded cDNA add 22 µl DEPC water, 4 µl 10×HY reaction buffer, 4 µl 10×biotin labeled ribonucleotides, 4 µl 10×DTT, 4 µl 10×RNase inhibitor mix and 2 µl 20×T7 RNA polymerase. All reagents are available in the BioArray High Yield RNA Transcript Labeling Kit from Enzo, distributed by Affymetrix, Inc. Gently mix and incubate at 37° C. for 4 hours, gently mixing every 30–45 min.

Use Rneasey Mini Kit from Qiagen, Valencia, Calif. according to the Rneasey mini Protocol for RNA Cleanup from the Qiagen handbook to clean up the cRNA. Add 60 µl of RNase-free water to the reaction from step 4 and elute from the column in 50 µl RNase-free water.

EXAMPLE THREE

Analysis using GeneChip® Probe Arrays

GeneChip® nucleic acid probe arrays are manufactured using technology that combines photolithographic methods and combinatorial chemistry. (See, e.g., the patents incorporated above.) In a preferred embodiment, over 280,000 different oligonucleotide probes are synthesized in a 1.28 cm×1.28 cm area on each array. Each probe type is located in a specific area on the probe array called a probe cell. Measuring approximately 24 μm×24 μm, each probe cell contains more than $10^7$ copies of a given oligonucleotide probe.

Probe arrays are manufactured in a series of cycles. A glass substrate is coated with linkers containing photolabile protecting groups. Then, a mask is applied that exposes selected portions of the probe array to ultraviolet light. Illumination removes the photolabile protecting groups enabling selective nucleotide phosphoramidite addition only at the previously exposed sites. Next, a different mask is applied and the cycle of illumination and chemical coupling is performed again. By repeating this cycle, a specific set of oligonucleotide probes is synthesized, with each probe type in a known physical location. The completed probe arrays are packaged into cartridges. These arrays are commercially available through Affymetrix Inc., Santa Clara, Calif.

The amplified RNA molecules are made as shown in Example 1 above. Labeled nucleotides are incorporated into the RNA during the IVT reaction. Then the RNA is fragmented and incubated with the array. The preferred label is biotin.

The hybridized probe array is stained with streptavidin phycoerythrin conjugate and scanned by the Hewlett-Packard (HP) GeneArray™ Scanner. (See U.S. Pat. Nos. 5,744,305 and 5,445,934.) The areas of hybridization are inputted into a computer and translated into information as to which nucleic acid sequences were present in the original sample. (See PCT/US00/20563.)

EXAMPLE FOUR

An example of an amplification using total RNA can be run in a process similar to that of Example 1. The 1st primer may be 5'GAGGCGGATTCACCGTCATTTTTTTTTTTT TTTTTTTTTTT 3' (SEQ. ID NO: 1) and the $2^{nd}$, primer, which contains a T7 promoter may be: 5'GGCCAGTGAAT-TGTAATACGACTCACTATAGGGAGGCGGATTCACC GTCA 3' (SEQ ID NO: 2). The cRNA transcripts will begin with the sequence 5'GGCGGAUUCACCGUCA 3' (SEQ ID NO: 3) so the cDNA synthesized using this RNA as a template will have the following sequence at the 3' end: 5 TGACGGTGAATCCGCC 3' (SEQ ID NO: 4). The $2^{nd}$ primer may then be used in the second round as the $3^{rd}$ primer.

The specific embodiments described above do not limit the scope of the present invention in any way as they are single illustrations of individual aspects of the invention. Functionally equivalent methods and components are within the scope of the invention. The scope of the appended claims thus includes modifications that will become apparent to those skilled in the art from the foregoing description.

We claim:

1. A method for the amplification of nucleic acid, said method comprising:
   (a) contacting mRNA having a poly (A) tail with a primer comprising poly d(T) and a second different sequence; and,
   generatng a first cDNA stand from the mRNA strand by extending the primer by reverse transcriptase and the appropriate nucleotide under the appropriate conditions, which creates a first RNA:DNA duplex;
   (b) denaturing the first RNA:DNA duplex;
   (c) forming a double stranded DNA;
   (d) adding a first promoter to the DNA by hybridizing a first promoter primer to the single stranded DNA;
   (e) forming a double stranded DNA promoter region by adding the appropriate reagents;
   (f) producing multiple copies of RNA comprsing at least part of said second different sequence from the DNA strand comprising the promoter;
   (g) contacting said multiple copies of RNA with random primers; and,
   generating a first DNA strand from the RNA by extending the primer by reverse transcriptase which creates a second RNA:DNA duplex;
   (h) denaturing the second RNA:DNA duplex; and,
   adding a second promoter to the DNA by hybridizing a second promoter primer to the single stranded DNA;
   (i) forming a double stranded DNA promoter region by adding the appropriate reagents; and,
   (j) producing multiple copies of RNA from the DNA strand comprising the promoter.

2. The method of claim 1 wherein steps (g–j) are repeated at least once.

3. The method of claim 1, wherein at least one of the enzymes used may be thermostable.

4. The method of claim 1 wherein said nucleic acid is selected from the group consisting of genomic DNA, cDNA, total RNA, poly(A)$^+$ RNA, and oligonucleotides.

5. The method of claim 1, wherein the first or second promoter primer is blocked fom extending in a 3' direction.

6. The method of claim 1 further comprising:
   contaeting said multiple copies of RNA produced in step (j) with a solid support comprising nucleic acid probes.

7. The method of claim 6 further comprising:
   detecting the presence or absence of hybridization of said multiple copies of RNA produced in step (j) to said nucleic acid probes on said solid support.

8. The method of claim 6 wherein said solid support comprising nucleic acid probes is selected from the group consisting of a nucleic acid probe array, a membrane blot, a microwell, a bead, and a sample tube.

9. The method of claim 1 wherein said nucleic acid is isolated from an eukaryotic cell or tissue.

10. The method of claim 9, wherein said eukaryotic cell or tissue is mammalian.

11. The method of claim 10 wherein said mammalian cell or tissue is human.

12. The method of claim 1 wherein said nucleic acid is isolated from a source selected from the group consisting of dissected tissue, microdissected tissue, a tissue subregion, a tissue biopsy sample, a cell sorted population, a cell culture, and a single cell.

13. The method of claim 1 wherein said nucleic acid is isolated from a cell or tissue source selected from the group consisting of brain, liver, heart, kidney, lung, spleen, retina, bone, lymnph node, endocrine gland, reproductive organ, blood, nerve, vascular tissue, and olfactory epithelium.

14. The method of claim 1 wherein said nucleic acid is isolated from a cell or tissue source selected from the group consisting of embryonic and tumorigenic.

15. The method of claim 1 wherein the method involves the use of an automated machine.

16. The method of claim 23 wherein said automated machine is selected from the group consisting of a thermocycler, an integrated reaction device, and a robotic delivery system.

17. A method for the amplification of nucleic acid, said method comprising:
   (a) contacting mRNA having a poly (A) tail with a primer comprising poly d(T) and a second sequence comprising a functional promoter sequence; and,
   generating a first cDNA strand from the mRNA strand by extending the first primer by reverse transcriptase and the appropriate nucleotides under the appropriate conditions, which creates a first RNA:DNA duplex;
   (b) denaturing the first RNA:DNA duplex;
   (c) contacting the DNA with random primers and forming a double stranded DNA with a functional promoter region;
   (d) producing multiple copies of RNA from the DNA strand comprising the promoter;
   (e) contacting said multiple copies of RNA with random primers; and, generating a first DNA strand from the RNA strand by extending the primer by reverse transriptase, which creates a second RNA:DNA duplex;
   (f) denaturing the second RNA:DNA duplex; and, adding a primer comprising poly d(T) and a promoter sequence;
   (g) forming a double stranded DNA;
   (h) forming a double stranded DNA promoter region by adding the appropriate reagents; and,
   (i) producing multiple copies of RNA from the DNA strand comprising the promoter.

18. The method of claim 17, wherein steps (e–i) are repeated at least once.

19. The method of claim 17, wherein said nucleic acid is selected from the group consisting of genomic DNA, cDNA, total RNA, poly(A)$^+$RNA, and oligonucleotides.

20. The method of claim 17, wherein the second sequence comprises a partial promoter sequence.

21. The method of claim 17, wherein said poly(A)+RNA is mRNA.

22. The method of claim 17, further comprising:

contacting said multiple copies of RNA produced in step (i) with a solid support comprising nucleic acid probes.

23. The method of claim 22 further comprising:

detecting the presence or absence of hybridization of said multiple copies of RNA produced in step (i) to said nucleic acid probes on said solid support.

24. The method of claim 22 wherein said solid support comprising nucleic acid probes is selected from the group consisting of a nucleic acid probe array, a membrane blot, a microwell, a bad, and a sample tube.

25. The method of claim 17 wherein said nucleic acid is isolated from an eukaryotic cell or tissue.

26. The method of claim 25, wherein said eukaryotic cell or tissue is mammalian.

27. The method of claim 26, wherein said mammalian cell or tissue is human.

28. The method of claim 17 wherein said nucleic acid is isolated from a source selected from the group consisting of dissected tissue, microdissected tissue, a tissue subregion, a tissue biopsy sample, a cell sorted population, a cell culture, and a single cell.

29. The method of claim 17 wherein said nucleic acid is isolated from a cell or tissue source selected from the group consisting of brain, liver, heart, kidney, lung, spleen, retina, bone, lymph node, endocrine gland, reproductive organ, blood, nerve, vascular tissue, and olfactory epithelium.

30. The method of claim 17 wherein said nucleic acid is isolated from a cell or tissue source selected from the group consisting of embryonic and tumorgenic.

31. The method of claim 17 wherein the method involves the use of an automated machine.

32. The method of claim 31 wherein said automated machine is selected from the group consisting of a thermocycler, an integrated reaction device, and a robotic delivery system.

33. A method for the amplification of nucleic acid, said method comprising:

(a) contacting mRNA having a poly (A) tail with a primer comprising poly d(T) operably linked to a functional promoter sequence; and, generating a first cDNA strand from the mRNA strand by extending the first primer by reverse transcriptase and the appropriate nucleotides under the appropriate conditions, which creates a first RNA:DNA duplex;

(b) denaturing the first RNA:DNA duplex;

(c) contacting the DNA with random primers and forming a double stranded DNA with a functional promoter region;

(d) producing multiple copies of RNA from the DNA strand comprising the promoter;

(e) contacting said multiple copies of RNA with random primers; and, generating a first DNA strand from the RNA strand by extending the primer by reverse transcriptase which creates a second RNA:DNA duplex;

(f) denaturing the second RNA:DNA duplex; and, adding a primer comprising poly d(T) and a promoter sequence wherein the primer is blocked from extending in a 3' direction;

(g) forming a double stranded DNA promoter region by adding the appropriate reagents; and, (h) producing multiple copies of RNA from the DNA strand comprising the promoter.

34. An amplified nucleic acid preparation comprising RNA obtained by the method of claim 33.

* * * * *

UNITED STATES PATENT AND TRADEMARK OFFICE
CERTIFICATE OF CORRECTION

PATENT NO. : 6,794,138 B1
APPLICATION NO. : 09/961709
DATED : September 24, 2001
INVENTOR(S) : Cao et al.

It is certified that error appears in the above-identified patent and that said Letters Patent is hereby corrected as shown below:

In Column 19:
    Claim 1, Line 19: Please replace "generatng" with --generating--
    Claim 1, Line 19: Please replace "stand" with --strand--
    Claim 1, Line 30: Please replace "comprsing" with --comprising--
    Claim 5, Line 54: Please replace "fom" with --from--
    Claim 6, Line 56: Please replace "contaeting" with --contacting--
In Column 20:
    Claim 13, Line 24: Please replace "lymnph" with --lymph--
    Claim 16, Line 31: Please replace "claim 23" with --claim 15--
    Claim 17, Line 54: Please replace "transriptase" with --transcriptase--
In Column 21:
    Claim 24, Line 15: Please replace "bad" with --bead--
    Claim 30, Line 34: Please replace "tumorgenic" with --tumorigenic--
In Column 22:
    Claim 33, Line 21: Please replace "(c)" with --(e)--

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO.         : 6,794,138 B1                                             Page 1 of 1
APPLICATION NO.    : 09/961709
DATED              : September 21, 2004
INVENTOR(S)        : Cao et al.

It is certified that error appears in the above-identified patent and that said Letters Patent is hereby corrected as shown below:

In Column 19:
    Claim 1, Line 19:  Please replace "generatng" with --generating--
    Claim 1, Line 19:  Please replace "stand" with --strand--
    Claim 1, Line 30:  Please replace "comprsing" with --comprising--
    Claim 5, Line 54:  Please replace "fom" with --from--
    Claim 6, Line 56:  Please replace "contaeting" with --contacting--

In Column 20:
    Claim 13, Line 24: Please replace "lymnph" with --lymph--
    Claim 16, Line 31: Please replace "claim 23" with --claim 15--
    Claim 17, Line 54: Please replace "transriptase" with --transcriptase--

In Column 21:
    Claim 24, Line 15: Please replace "bad" with --bead--
    Claim 30, Line 34: Please replace "tumorgenic" with --tumorigenic--

In Column 22:
    Claim 33, Line 21: Please replace "(c)" with --(e)--

This certificate supersedes Certificate of Correction issued August 7, 2007.

Signed and Sealed this

Twenty-eighth Day of August, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 42
<212> TYPE: DNA
<213> ORGANISM: artificial sequence
<220> FEATURE:
<223> OTHER INFORMATION: synthetic oligonucleotide

<400> SEQUENCE: 1
gaggcggatt caccgtcatt tttttttttt tttttttttt tt                    42

<210> SEQ ID NO 2
<211> LENGTH: 50
<212> TYPE: DNA
<213> ORGANISM: artificial sequence
<220> FEATURE:
<223> OTHER INFORMATION: synthetic oligonucleotide

<400> SEQUENCE: 2
ggccagtgaa ttgtaatacg actcactata gggaggcgga ttcaccgtca            50

<210> SEQ ID NO 3
<211> LENGTH: 16
<212> TYPE: RNA
<213> ORGANISM: artificial sequence
<220> FEATURE:
<223> OTHER INFORMATION: synthetic oligonucleotide

<400> SEQUENCE: 3
ggcggauuca ccguca                                                 16

<210> SEQ ID NO 4
<211> LENGTH: 16

-continued

```
<212> TYPE: DNA
<213> ORGANISM: artificial sequence
<220> FEATURE:
<223> OTHER INFORMATION: synthetic oligonucleotide

<400> SEQUENCE: 4
tgacggtgaa tccgcc                                                    16
```